United States Patent
Satoh et al.

(10) Patent No.: US 9,107,651 B2
(45) Date of Patent: Aug. 18, 2015

(54) TEST APPARATUS AND METHOD OF OBSERVING BIOPSY SPECIMEN SAMPLED BY USING TEST APPARATUS

(71) Applicant: CANON KABUSHIKI KAISHA, Tokyo (JP)

(72) Inventors: Shuya Satoh, Yokohama (JP); Hiroyuki Hashimoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/289,504

(22) Filed: May 28, 2014

(65) Prior Publication Data

US 2014/0354987 A1    Dec. 4, 2014

(30) Foreign Application Priority Data

May 29, 2013    (JP) .................................. 2013-113230

(51) Int. Cl.
*A61B 10/02*    (2006.01)
*A61B 5/00*    (2006.01)

(52) U.S. Cl.
CPC ........... *A61B 10/0266* (2013.01); *A61B 5/0075* (2013.01); *A61B 5/0086* (2013.01); *A61B 5/6848* (2013.01); *A61B 10/0275* (2013.01)

(58) Field of Classification Search
CPC ........... A61B 10/0233; A61B 10/0266; A61B 10/0275; A61B 2010/0225
USPC .................................................. 600/562–567
See application file for complete search history.

(56) References Cited

U.S. PATENT DOCUMENTS 8,690,793 B2 *   4/2014   Ranpura et al. ............... 600/562
8,771,200 B2 *   7/2014   Thompson et al. ........... 600/564
8,858,461 B2 *  10/2014   Persat .......................... 600/562

FOREIGN PATENT DOCUMENTS

JP    2002-524780 A    8/2002

OTHER PUBLICATIONS

Verkooijen, et al., "Diagnostic accuracy of large-core needle biopsy for non-palpable breast disease: a meta-analysis", British Journal of Cancer, (2000), 82(5), pp. 1017-1021.
Ozeki, et al., "High-speed molecular spectral imaging of tissue with stimulated Raman scattering", Nature Photonics, Dec. 2012, vol. 6, pp. 845-851.

* cited by examiner

*Primary Examiner* — Max Hindenburg
(74) *Attorney, Agent, or Firm* — Canon U.S.A., Inc. IP Division

(57) ABSTRACT

A test apparatus includes a biopsy needle for sampling a biopsy specimen. The biopsy needle includes a specimen holder that holds the sampled biopsy specimen, and an optical window disposed in the specimen holder and configured to allow optical detection. A biopsy specimen held by the specimen holder of the test apparatus is measured by using a third-order nonlinear Raman microscope.

20 Claims, 7 Drawing Sheets

TEST APPARATUS AND METHOD OF OBSERVING BIOPSY SPECIMEN SAMPLED BY USING TEST APPARATUS

BACKGROUND OF THE INVENTION

1. Field of the Invention

The present invention relates to a test apparatus and to a method of observing a biopsy specimen sampled by using the test apparatus. In particular, the present invention relates to a test apparatus for sampling a biopsy specimen from living tissue that can be used for making a pathological sample and for histopathological examination, and to a method of observing a specimen sampled by using the test apparatus.

2. Description of the Related Art

In medical institutes and hospitals, naked-eye observation of living tissue and observation of living tissue using an optical microscope or an electron microscope are widely performed.

In particular, pathological diagnosis is an important medical activity for determining the presence, the type, and the state of a lesion. In pathological analysis, a tissue specimen is sampled from a patient for whom cancer, a premalignant condition, or the like is suspected, and the tissue specimen is histopathologically examined by microscopic observation.

In order to reduce physical strain and mental strain on a patient, it is required that sampling of a specimen be minimally invasive and a diagnostic result be obtained in a short time by starting observation of the specimen as early as possible.

For example, needle biopsy has been increasingly used as a method for making pathological diagnosis less invasive. Biopsy is a procedure in which a part of body tissue of a patient, which will be used as a specimen, is sampled in order to diagnose or screen a disease.

In the following description, a method of using a needle for sampling a biopsy specimen will be referred to as "needle biopsy", and a needle used for needle biopsy will be referred to as a "biopsy needle".

Examples of biopsy needles include a hollow single-tube needle, a needle including an outer tube and an inner tube, and a needle including an outer tube and an inner needle. Each of the biopsy needles includes a cutter for cutting tissue and a specimen holder.

Sampling of a specimen by needle biopsy has been widely used recently because diagnostic information equivalent to that of surgical biopsy can be obtained less invasively by needle biopsy.

With such a method, even tissue that is located in a deep portion of the body of a patient can be percutaneously sampled, as described in British Journal of Cancer 82, 1017-1021, 2000.

Making specimen sampling less invasive provides, for example, the following advantages: reducing patient recovery time, reducing pain, reducing surgery time, reducing cost, reducing the risk of impairing adjacent body tissue, and suppressing damage to the anatomical appearance of a patient.

Examples of a method for reducing the time required for processing a specimen, which are under study, include techniques for observing an unstained tissue specimen. Nature Photonics 6, 845-851, 2012 describes a method of obtaining an image of an unstained tissue by slicing tissue removed from a living body in a frozen state, making a specimen by clamping the sliced tissue between two flat glass plates, and by observing the specimen using a stimulated Raman microscope.

Stimulated Raman scattering, which is a third-order nonlinear optical effect, is a phenomenon in which the energy of light having a shorter wavelength shifts to light having a longer wavelength when the light of the two wavelengths and molecular vibration of molecules interact with each other and the difference in the wavelengths of light coincides with the frequency of the molecular vibration. By using a stimulated Raman microscope, a signal generated due to stimulated Raman scattering caused by a specific molecular vibration of molecules in a specimen can be detected and the signal can be displayed as a contrast image. In other words, with such a system, an image representing information of the shape and the composition of a tissue specimen can be presented to a user without performing a staining process, such as hematoxylin and eosin stain or special stain.

Reduction in specimen processing time provides, for example, the following advantages: reducing or eliminating mental strain on a patient caused by the length of time before a diagnostic result is provided to the patient, which is mainly due to the time required for specimen processing; and reducing cost.

Examples of another method for reducing the specimen processing time include a combination of a specimen sampling method and a technique for observing an unstained tissue specimen.

For example, PCT Japanese Translation Patent Publication No. 2002-524780 describes a system for obtaining a tissue image by using a transparent trocar as a specimen sampling apparatus and as a tissue observation cassette.

With this system, a specimen of tissue is encapsulated in a transparent cassette while the specimen is being cut off the tissue by using a trocar, and an electro-optical imaging device is used. Therefore, it is possible to observe an unstained tissue specimen while considerably reducing the time required for sampling and processing the specimen.

However, even with the existing methods described above, it is still difficult to make specimen sampling less invasive while reducing the specimen processing time, and these methods have the following problems.

With the needle biopsy method described in British Journal of Cancer 82, 1017-1021, 2000, the time required for performing the entire procedure is not particularly reduced, although this method is effective in making specimen sampling less invasive.

In other words, with this method, the time required for processing a sampled specimen into a microscope specimen is considerably longer than the time required for specimen sampling and diagnosis. Therefore, even if the specimen sampling time is reduced by omitting incision and closure, the effect on the entire procedure is small and the time required for the entire procedure cannot be reduced considerably.

For example, in order to make a tissue specimen used for final diagnosis, it takes about 24 to 72 hours to perform a plurality of steps including chemical fixation, embedding, slicing, fixing to an observation substrate, and staining.

With the system described in Nature Photonics 6, 845-851, 2012, it is necessary to sample a specimen by cutting and slicing tissue in order to observe a specimen that is not located at a position that can be observed in vivo from the body surface or from the inside of a tubular organ.

Therefore, although the specimen processing time can be reduced by omitting a staining process, the time required for retrieving a specimen from a biopsy apparatus and the time required for slicing the specimen cannot be reduced. As a result, the method has a problem in that the effect of reduction in the total time for obtaining a diagnostic result is limited.

Moreover, improvement of invasiveness of specimen sampling is not mentioned at all.

The system described in PCT Japanese Translation Patent Publication No. 2002-524780 has a problem in that the system is highly invasive as a means for specimen sampling.

A trocar, which is a surgical device that is used to insert another surgical device into a body cavity, is used by penetrating a sharp end of an obturator through a body wall and by leaving a hollow cannula, from which the obturator has been removed, in a retracted portion. A trocar has comparatively large outside diameter and inside diameter so that the other surgical device can be smoothly inserted.

With a general biopsy needle, which has an outside diameter less than 5 mm and mostly about 2 mm, strain on a patient can be minimized by removing the biopsy needle soon after the specimen has been sampled. In contrast, strain on a patient is considerably large when a trocar is used as a specimen sampling device.

SUMMARY OF THE INVENTION

The present invention provides a test apparatus with which invasiveness of sampling of a biopsy specimen can be improved and observation of a sampled biopsy specimen can be started in a short time, and a method of observing a biopsy specimen obtained by using the test apparatus.

According to a first aspect of the present invention, a test apparatus includes a biopsy needle for sampling a biopsy specimen. The biopsy needle includes a specimen holder that holds the sampled biopsy specimen, and an optical window disposed in the specimen holder and configured to allow optical detection.

According to a second aspect of the present invention, a method of observing a biopsy specimen sampled by using a test apparatus includes optically observing, by using the test apparatus according to the first aspect, a biopsy specimen held by the specimen holder.

Further features of the present invention will become apparent from the following description of exemplary embodiments with reference to the attached drawings.

BRIEF DESCRIPTION OF THE DRAWINGS

FIG. 3A is a sectional side view of a Tru-cut biopsy needle (which is not holding a specimen), FIG. 3B is a sectional top view of a Tru-cut biopsy needle having an optical window (which is holding a specimen), and FIG. 3C is a sectional side view of a Tru-cut biopsy needle having an optical window and a reflection layer (which is holding a specimen).

FIG. 4A illustrates the positional relationship among an optical axis, an optical window, and a specimen in transmission measurement, and FIG. 4B illustrates the positional relationship among an optical axis, an optical window, a specimen, and a reflection layer in reflection measurement.

FIG. 5A is a sectional side view of an aspiration biopsy needle including a specimen holder having an optical window and a channel (which is not holding a specimen), and FIGS. 5B to 5E are each a sectional side view of a Tru-cut biopsy needle having an optical window and a channel (which is not holding a specimen).

FIG. 6A is a cross-sectional view of a biopsy needle having a multi-element structure in which channels are formed in an inner needle, FIG. 6B is a cross-sectional view of a biopsy needle having a multi-element structure in which a channel is formed in an inner needle and a channel is formed in an outer peripheral portion of the inner needle, and FIG. 6C is a cross-sectional view of a biopsy needle having a multi-element structure in which a channel is formed in an inner needle and a channel is formed in a gap between the inner needle and an outer tube.

DESCRIPTION OF THE EMBODIMENTS

Figure 1:
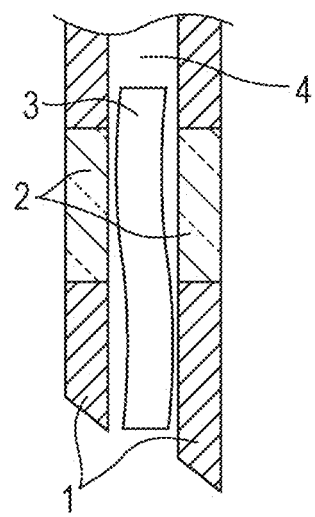
FIG. 1 is a sectional side view of an aspiration biopsy needle, having an optical window, of a test apparatus according to a first exemplary embodiment of the present invention.

A test apparatus according to an exemplary embodiment of the present invention includes a biopsy needle for sampling a biopsy specimen. An optical window is disposed in a part of the biopsy needle so that optical detection can be performed at a specimen holder in the biopsy needle.

Preferably, the optical window is transmissive to visible light and near-infrared light in the wavelength range from the visible region to 1400 nm. More preferably, the optical window is transmissive to long-wavelength visible light and near-infrared light in the wavelength range from 700 nm to 1400 nm.

Preferably, the ratio of the thickness of the optical window to the thickness of a tubular member of the biopsy needle coupled to the optical window is less than 2. More preferably, the thickness of the optical window is less than or equal to the sum of 0.1 mm and the thickness of a wall of the tubular member, and still more preferably the thickness of the optical window is equal to or less than the thickness of the tubular member.

The optical window may be disposed so that the optical axis of light that enters the optical window for optical detection or imaging intersects the optical window at two positions that are respectively on the distal side and on the proximal side of the specimen in the propagation direction of the light. Alternatively, the optical window may be disposed so that the optical axis of light that enters the optical window for optical detection or imaging intersects the optical window at one position that is on the proximal side of the specimen in the propagation direction of the light. In the latter case, a reflection layer may be disposed at a position that is on the distal side of the specimen in the propagation direction.

A channel for introducing a measurement auxiliary liquid into the specimen holder or discharging the measurement auxiliary liquid from the specimen holder may be formed in the specimen holder of the test apparatus according to an exemplary embodiment of the present invention. The channel may have an opening formed in a wall surface of the specimen holder and the opening may have a structure for preventing falling of a specimen and for preventing a specimen from blocking the opening.

A method of observing a biopsy specimen sampled by using the test apparatus according to an exemplary embodiment of the present invention includes optically observing a specimen held by the specimen holder in the biopsy needle.

The optical observation may be performed by using a third-order nonlinear Raman microscope. In particular, the third-order nonlinear Raman microscope may be a stimulated Raman microscope.

The optical observation may be performed before the specimen contacts a measurement auxiliary liquid introduced through a channel formed in a specimen holder of the test apparatus, may be performed after the specimen has contacted the measurement auxiliary liquid, or may be performed at least once before the biopsy specimen contacts the measurement auxiliary liquid and at least once after the biopsy specimen has contacted the measurement auxiliary liquid.

Hereinafter, the exemplary embodiments will be described in detail with reference to the drawings. The present invention is not limited to the exemplary embodiments.

(First Exemplary Embodiment)

Referring to FIGS. 1 to 4B, test apparatuses including biopsy needles according to a first exemplary embodiment of the present invention will be described. Each of the biopsy needles may be a needle including a hollow single-tube, a needle including an outer tube and an inner tube, or a needle including an outer tube and an inner needle. Each of the biopsy needles includes a cutter for cutting tissue and a specimen holder.

Figure 2:
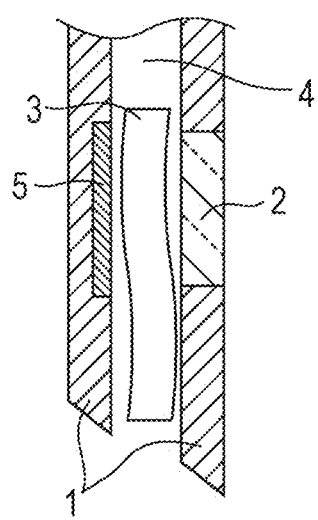
FIG. 2 is a sectional side view of an aspiration biopsy needle, having an optical window and a reflection layer, of the test apparatus according to the first exemplary embodiment of the present invention.

FIGS. 1 and 2 each illustrate a single-tube hollow needle used for aspiration biopsy.

Figure 3A:
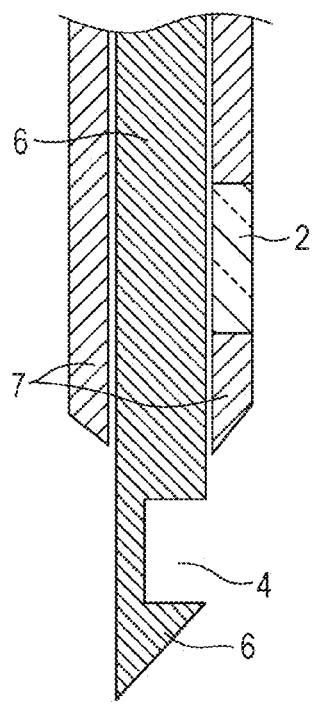
FIGS. 3A to 3C each illustrate a biopsy needle of the test apparatus according to the first exemplary embodiment of the present invention.
Figure 3B:
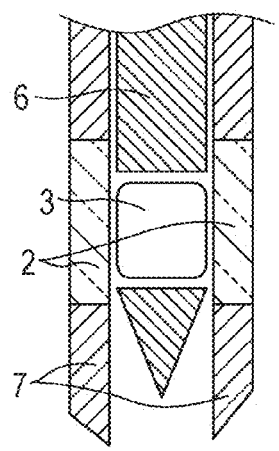
Figure 3C:
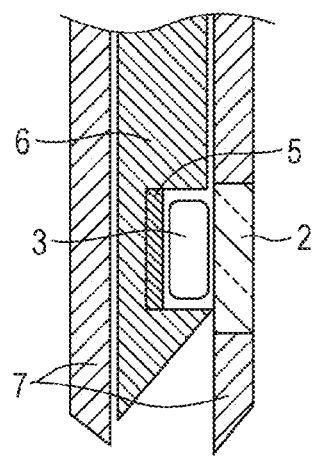

FIGS. 3A to 3C each illustrate a biopsy needle having a multi-element structure, which is an example of a Tru-cut biopsy needle used for core biopsy and the like.

FIG. 3A is a sectional side view of a Tru-cut biopsy needle (which is not holding a specimen).

FIG. 3B is a sectional top view of a Tru-cut biopsy needle including an optical window (which is holding a specimen).

FIG. 3C is a sectional side view of a Tru-cut biopsy needle including an optical window and a reflection layer (which is holding a specimen).

A test apparatus according to the present exemplary embodiment includes an optical window 2 or an optical window 2 and a reflection layer 5; and a tubular member 1 or an outer tube 7 that is slideable. The optical window 2 is or the optical window 2 and the reflection layer 5 are disposed at a part of a side surface of the tubular member 1 or the outer tube 7.

For example, in a case where a biopsy needle includes a tubular member, a specimen holder may be formed in a hollow portion of the tubular member, and an optical window may be formed in a wall portion of the tubular member.

In a case where a biopsy needle includes an outer tube and an inner tube that is slideable along the outer tube, a specimen holder may be formed in the inner tube and an optical window may be formed in a wall portion of the outer tube.

The test apparatus is configured so that a specimen (sampled biopsy specimen) 3 can be removed from tissue by using a sharp end of the tubular member 1 or the outer tube 7, and so that the specimen 3 held by a specimen holder 4 can be observed through the optical window 2.

Examples of biopsy methods that are mainly used at present include aspiration needle biopsy and core needle biopsy. In general, a biopsy needle having a diameter that is sufficiently small but is not too small to hinder intended diagnosis is used.

For example, for diagnosis of breast cancer, a biopsy needle of 14 G (outside diameter 2.1 mm/inside diameter 1.6 mm/wall thickness 0.26 mm) and having a tissue sampling groove of about 20 mm, or a biopsy needle having a similar size is used.

To sample bone marrow, a relatively thick biopsy needle of 8 G (outside diameter 4.2 mm/inside diameter 3.4 mm/wall thickness 0.38 mm) may be used. To sample liver tissue, a relatively thin biopsy needle of about 22 G (outside diameter 0.7 mm/inside diameter 0.4 mm) may be used.

Examples of known methods for observing unstained tissue include a Raman scattering method, which is a method of analyzing a spectrum obtained by separating non-linear Raman scattered light emitted from a specimen irradiated with a laser beam.

Because Raman scattered light emitted from a specimen is specific to a substance, it is possible to analyze molecules constituting the specimen. Imaging apparatuses using stimulated Raman scattering, hyper Raman scattering, and coherent anti-Stokes Raman scattering (CARS) have been proposed.

By using such a system, an image of unstained tissue can be obtained in principle. In particular, a stimulated Raman microscope may be particularly used, because a stimulated Raman microscope can provide molecular information having a sensitivity or an S/N ratio that are significantly higher than those of other detection methods for detecting molecular vibrations.

The Raman scattering method may be used for optical observation according to the present invention. However, this is not a limitation. Optical coherence tomography, with which an OCT image can be obtained, may be used to observe unstained tissue. Fluorescence imaging using a fluorescence microscope may be used to observe stained tissue.

Existing biopsy apparatuses are designed on the assumption that the specimen 3 held by the specimen holder 4 is separated and retrieved from the apparatus and the specimen is subjected to specimen processing in a postprocessing step.

Therefore, the tubular member 1 is mainly made of a stainless steel, titanium, a nickel-chrome alloy, a titanium alloy, or the like, because such a material has a sufficiently high mechanical strength with a small thickness and can be easily machined.

However, such a material is opaque in a wide wavelength range including the visible region and the near-infrared region, and therefore it is difficult to measure or observe the specimen 3 held in the specimen holder 4 by using an optical apparatus from the outside.

In contrast, with the present exemplary embodiment, the optical window 2 is formed in a part of a side surface of the tubular member 1, and therefore it is possible to perform optical observation through the optical window.

To observe living tissue using a microscope, light in the visible region or light in the near-infrared region is usually used.

In general, the near-infrared region corresponds to a wavelength range of about 750 to 2500 nm. The three-dimensional structure of living tissue can be effectively observed by using visible light having a long wavelength or light in the near-infrared region. It is particularly desirable that light in such regions be transmitted. For example, to observe a position in a living body below the surface of the living body, light in a region of about 700 to 1400 nm is usually used, because such light is relatively less influenced by absorption by water molecules.

It is necessary that the optical window 2 transmits light in a wavelength range that is suitable for an observation device used.

The transmittance is preferably 50% or greater, more preferably 90% or greater, and still more preferably 95% or greater. If the transmittance is low, a part of light entering the optical window may be converted into heat and the heat may influence the optical characteristics and the shape of the optical window.

Examples of a material having a relatively high transmittance for light in the visible region to the near-infrared region include inorganic materials such as glass, quartz, and sapphire; and organic materials, such as polyethylene, polyvinyl chloride, polycarbonate, polyethylene terephthalate, polypropylene, polystyrene, and an amorphous fluorocarbon polymer.

Examples of a material having a relatively high transmittance for light in the near-infrared region include inorganic materials, such as glass, quartz, sapphire, and chalcogenide glass; and organic materials, such as polyethylene, polyvinyl chloride, polycarbonate, polyethylene terephthalate, polypropylene, polystyrene, and an amorphous fluorocarbon polymer. One of such materials or a combination of such materials can be used.

A problem to be solved when mounting the optical window 2 in the tubular member 1 is how to mount the optical window 2 for observing the specimen 3, which is held by the specimen holder 4 of the biopsy needle, without affecting the function of the biopsy needle.

The optical window 2 may be attached to the tubular member 1 by using a known method such as adhesive boning, diffused junction, fitting, or the like.

The thickness of the optical window 2 is preferably less than twice the thickness of a wall of the tubular member 1, more preferably less than or equal to the sum of 0.1 mm and the thickness of the wall of the tubular member 1, and still more preferably less than or equal to the thickness of the wall of the tubular member 1.

This is because, if the optical window 2 protrudes radially outward from the tubular member 1, the locus of the biopsy needle or friction generated when the biopsy needle is inserted into the body tissue may be affected and unwanted damage may be inflicted on tissue located adjacent to the biopsy needle.

Moreover, if the optical window 2 protrudes radially inward from the tubular member 1, damage may be inflicted on the specimen 3 and diagnosis may become difficult. If the thickness of the optical window 2 exceeds twice the thickness of the tubular member 1, it becomes more likely that such problems occur.

Figure 4A:
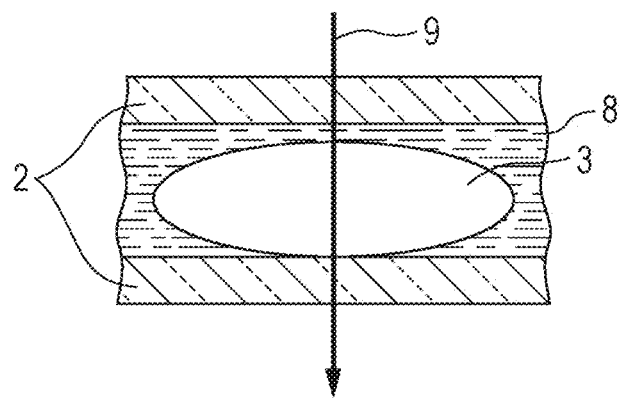
FIGS. 4A and 4B each illustrate the structure of a biopsy needle according to the first exemplary embodiment of the present invention.

As illustrated in FIG. 4A, the optical window may be disposed so that an optical axis 9 of light that enters the optical window 2 for optical detection or imaging intersects the optical window 2 at two positions that are respectively on the distal side and on the proximal side of the specimen 3 in the propagation direction of the light. In this case, it is possible to perform transmission-type observation.

The optical window may include two independent members, may be one curved member, or may be a part of a cylindrical member.

Although a smaller curvature of the optical window 2 is advantageous for suppressing aberration, the shape of the optical window 2 should be appropriately determined as necessary.

A gap between the specimen 3 and the optical window 2 and a gap between the objective lens and the optical window 2 may be filled with a refractive index matching liquid 8. By doing so, even if the optical window 2 has a large curvature, it is possible to perform a desired observation without causing a problem of aberration.

Figure 4B:
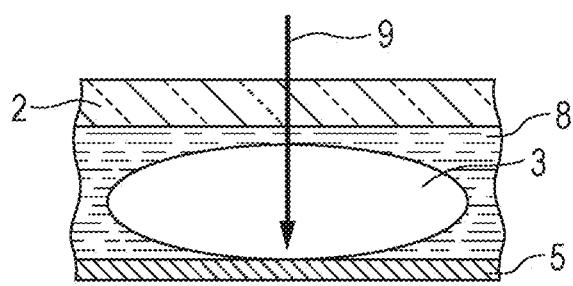

As illustrated in FIG. 4B, the optical window 2 may be disposed so that the optical axis 9 of light that enters the optical window 2 for optical detection or imaging intersects the optical window 2 at one position that is on the proximal side of the specimen 3 in the propagation direction of the light, and the reflection layer 5 for reflecting near-infrared light may be disposed at a position that is on the distal side of the specimen 3 in the propagation direction. In this case, it is possible to perform reflection-type observation easily.

Although a smaller curvature of the optical window 2 is advantageous for suppressing aberration, the shape of the optical window 2 should be appropriately determined as necessary.

By disposing the near-infrared light reflection layer, signal sensitivity is improved due to so-called epi-detection, and imaging of a signal can be easily performed. A gap between the specimen 3 and the optical window 2 and a gap between the objective lens and the optical window 2 may be filled with the refractive index matching liquid 8. By doing so, even if the optical window 2 has a large curvature, it is possible to perform a desired observation without causing a problem of aberration.

(Second Exemplary Embodiment)

Referring to FIGS. 5A to 6C, test apparatuses according to a second exemplary embodiment, in which channels are formed in the specimen holder of the biopsy needle, will be described.

With the present exemplary embodiment, desired observation can be performed by causing a measurement auxiliary liquid, for adjusting the state of a specimen, to contact the specimen through a channel 10 formed in the specimen holder 4 of the biopsy needle.

Figure 5A:
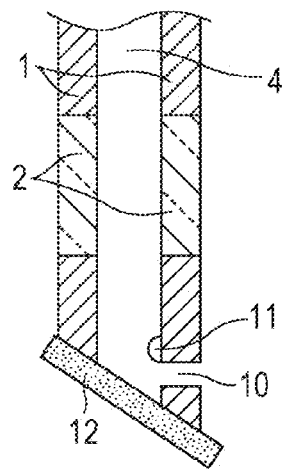
FIGS. 5A to 5E each illustrate a biopsy needle of a test apparatus according to a second exemplary embodiment of the present invention.

The shape and the position of the channel 10 should be appropriately determined so that the channel 10 would not impair the strength of the biopsy needle and so that the measurement auxiliary liquid can be introduced and discharged efficiently. However, as illustrated in FIG. 5A, a hollow needle itself, which has a tail end that is closed and a side surface in which an opening is formed, may be used as the channel 10. In this case, a head end of the hollow needle is sealed with a sealing member 12 when the hollow needle is used as the channel 10 after a specimen has been sampled.

Figure 5B:
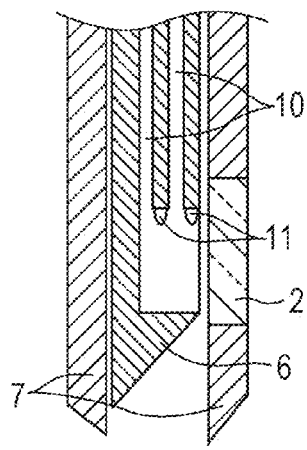
Figure 5C:
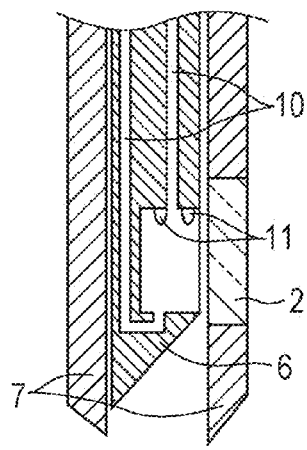
Figure 5D:
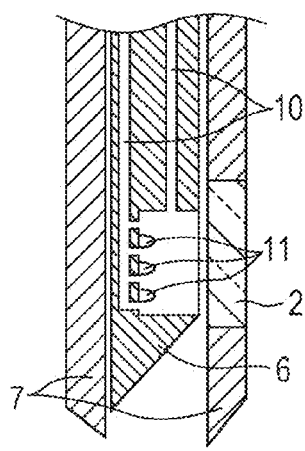
Figure 5E:
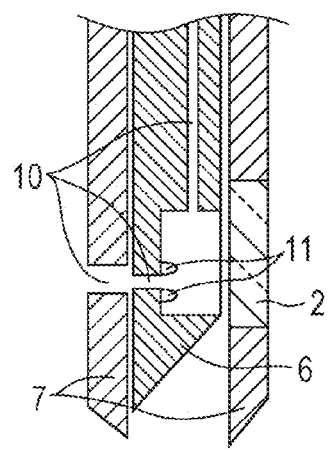

As illustrated in FIGS. 5B to 5D, a biopsy needle may include an outer tube and an inner needle 6 that is slideable along the outer tube, and at least one channel for introducing a measurement auxiliary liquid and at least one channel for discharging the measurement auxiliary liquid may be formed in the inner needle 6. The channels in the specimen holder may have openings in only one wall surface in the specimen holder, at least one opening in each of two opposing wall surfaces in the specimen holder, or at least one opening in each of two or three non-opposing surfaces in the specimen holder. As illustrated in FIG. 5E, an opening may be formed in a side portion of the outer tube 7, and the opening may be connected to an opening formed in the specimen holder 4 of the inner needle 6.

Figure 6A:
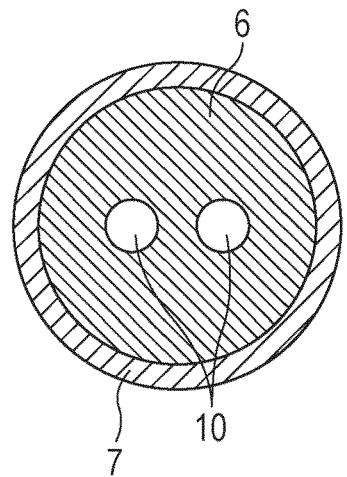
FIGS. 6A to 6C each illustrate the structure of a biopsy needle of the test apparatus according to the second exemplary embodiment of the present invention.
Figure 6B:
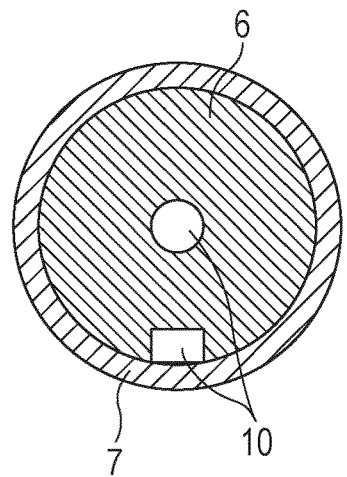
Figure 6C:
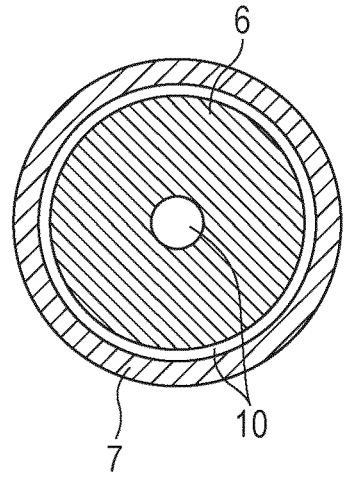

As illustrated in FIGS. 6A to 6C, the channels 10, which are used for introducing and discharging a measurement auxiliary liquid, may be formed in the inner needle, may be formed as a recess in an outer peripheral portion of the inner needle, may be formed as a gap between the outer tube and the outer periphery of the inner needle, or may be formed as a combination of such structures. The direction in which a measurement auxiliary liquid flows through each of the channels may be appropriately determined as necessary.

In the case where channels are formed in the inner needle, it is necessary to maintain the strength of the inner needle. Therefore, preferably, the sum of the areas of cross sections of the channels is less than 80% of the area of a cross section of the inner needle, and more preferably, less than 50% of the area of the cross section of the inner needle, the cross sections being parallel to the short axis of the inner needle.

Protrusions 11 may be formed near the openings of the channel 10. By doing so, the openings are prevented from becoming closed as a specimen is moved while the measurement auxiliary liquid is introduced and discharged, and therefore the measurement liquid can be efficiently supplied to the specimen holder.

(Third Exemplary Embodiment)

Figure 7:
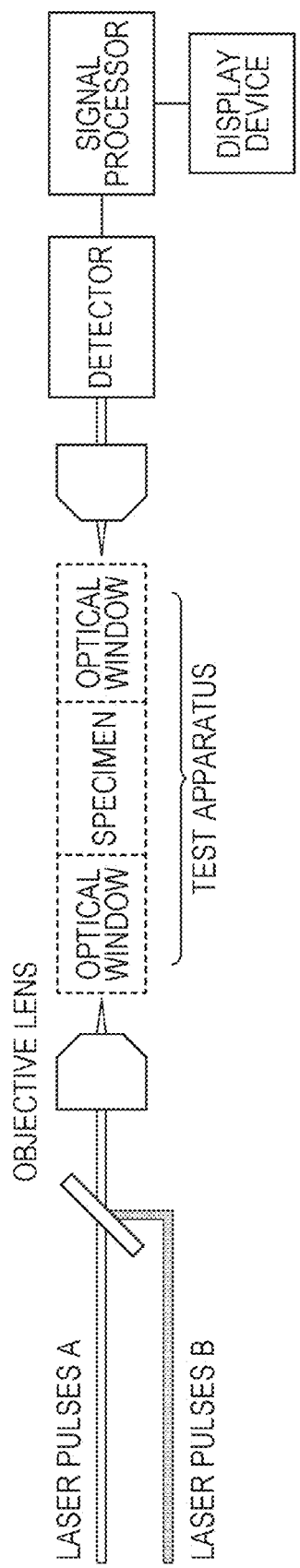
FIG. 7 illustrates an example of a method of observing a biopsy specimen held by a biopsy needle by using a stimulated Raman microscope according to a third exemplary embodiment of the present invention.

Referring to FIG. 7, a third exemplary embodiment will be described. The third embodiment is an example of a method of performing transmission-type observation of the specimen 3 held by the specimen holder 4 of the biopsy needle by using a third-order nonlinear Raman microscope. FIG. 7 is a block diagram illustrating the present exemplary embodiment.

Two laser beams having different wavelengths are focused on a specimen through a first objective lens.

An optical signal representing Raman scattering that occurs at the focal position passes through a second objective lens, which is disposed opposite the first objective lens, and the light signal is obtained by using a detector.

A signal processor performs spectrum analysis and image reconstruction, and information is provided to a user through a display device.

Test apparatuses according to the present invention that can be used for transmission-type observation are illustrated in FIGS. 1, 3B, 4A, and 5A. One of the test apparatuses is disposed at the position of a specimen shown in FIG. 7. In a case of performing reflection-type measurement, only one of the windows may be open.

A measurement process performed by using the test apparatuses according to the present invention shown in FIGS. 5A to 5E may include causing a specimen to contact a measurement auxiliary liquid for adjusting the state of the specimen.

The measurement auxiliary liquid may be a buffer solution, a preservative solution, a chemical fixative solution, or the like. By causing a specimen to contact such a liquid, the properties of the specimen can be stabilized and desired observation can be performed. The measurement auxiliary liquid may be a buffer solution whose temperature, pH, and gas pressure have been adjusted or a bioactive solution. By performing measurement in a state in which the specimen is in contact with such a liquid, information regarding change in the state of the specimen can be obtained. If cells or tissue fragments adhere to the specimen, it is difficult to observe a specimen. Even in such a case, desired observation can be performed by cleaning the specimen using a buffer solution or the like. For example, in order to clean a specimen sampled from fat tissue, it is particularly effective to use a buffer solution including a surfactant as a measurement auxiliary liquid. In this case, non-ionic surfactants, such as Tween20 and Tween80, may be used. A measurement auxiliary liquid may also function as a refractive index matching liquid illustrated in FIGS. 4A and 4B.

In measurement performed by using third-order non-linear Raman scattering, the shape of the optical window 2 should be appropriately determined so that aberration generated due to the difference in the refractive indices when two laser beams used pass through the optical window is 10% or less.

If the aberration exceeds 10%, the frequency of occurrence of Raman scattering in a finite time is greatly influenced by a combination of the wavelengths of incident laser beams, and, as a result, the quantity of obtained information may be reduced.

Figure 8:
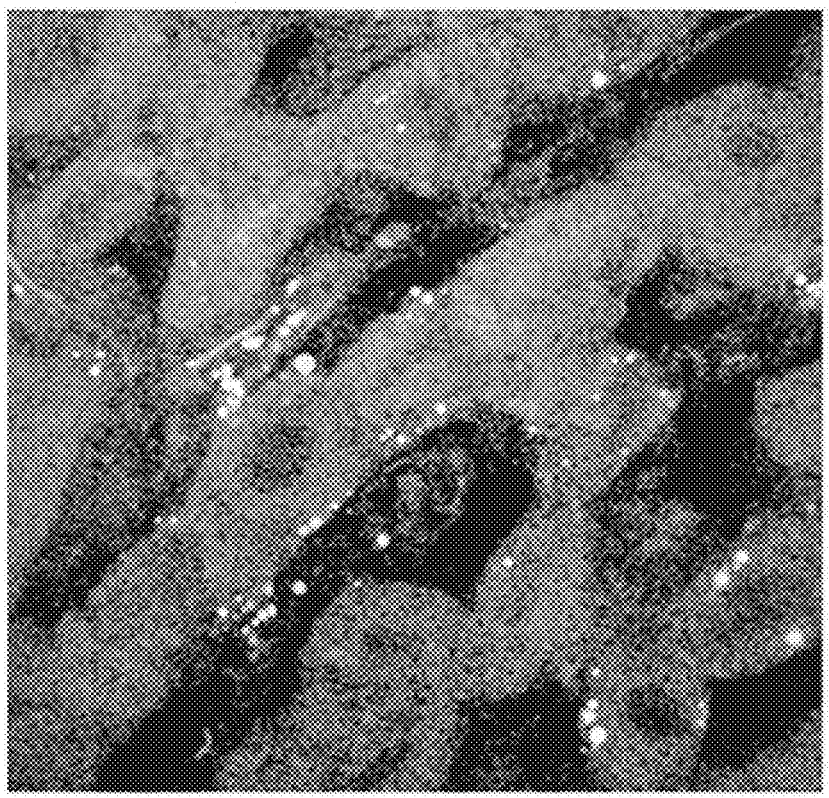
FIG. 8 illustrates an example in which a signal obtained by using a stimulated Raman microscope is displayed as a stimulated Raman microscope image (2850 cm-1) according to the third exemplary embodiment of the present invention.

A signal obtained by using a third-order nonlinear Raman microscope can be directly formed into a contrast image as shown in FIG. 8.

Moreover, a result obtained by performing analysis and evaluation using a combination of information for a plurality of wavelengths can be displayed.

A stimulated Raman microscope may be particularly used because it provides molecular information that has a sensitivity or an S/N ratio that are significantly higher than those obtained by using other methods for detecting molecular vibration.

A high-speed observation, which is a characteristic of a stimulated Raman microscope, is advantageous in, for example, measuring and imaging the structure of living tissue.

In particular, to perform imaging of a three-dimensional structure, a laser beam having a wavelength in the near-infrared region, which can efficiently pass through a specimen, may be particularly used.

In a case where the optical window is transmissive to light from the visible region to the near-infrared region, the degree of freedom of selecting a light source is increased. Therefore, complex information can be easily obtained and the value of information provided to a user can be increased.

For example, by using two or more light sources, a signal representing molecular excitation due to visible light and a signal representing Raman scattering due to near-infrared light can be obtained through the optical window of the test apparatus.

Moreover, various pieces of information obtained by using different measurement methods can be combined by using a signal processor, analysis and evaluation can be performed on the information, and the results of the analysis and evaluation can be displayed.

When performing observation by using the apparatus according to the present invention, the sharp end of the apparatus may be covered with a protector for safety.

With the present invention, it is possible to provide a test apparatus with which invasiveness of sampling of a biopsy specimen can be improved and observation of a sampled biopsy specimen can be started in a short time, and it is possible to provide a method of observing a biopsy specimen obtained by using the test apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application Claims the benefit of Japanese Patent Application No. 2013-113230, filed May 29, 2013, which is hereby incorporated by reference herein in its entirety.

What is claimed is:

1. A test apparatus comprising:
a biopsy needle for sampling a biopsy specimen,
wherein the biopsy needle includes
a specimen holder that holds the sampled biopsy specimen, and
an optical window disposed in the specimen holder and configured to allow optical detection of the biopsy specimen.

2. The test apparatus according to claim 1,
wherein the biopsy needle includes a tubular member, and
wherein the specimen holder is formed in a hollow portion of the tubular member, and the optical window is formed in a wall portion of the tubular member.

3. The test apparatus according to claim 2,
wherein a thickness of the optical window is less than twice a thickness of the wall portion of the tubular member.

4. The test apparatus according to claim 2,
wherein a thickness of the optical window is less than or equal to the sum of 0.1 mm and a thickness of the wall portion of the tubular member.

5. The test apparatus according to claim 1,
wherein the biopsy needle includes an outer tube and an inner tube or an inner needle, the inner tube or the inner needle being slidable along the outer tube, and
wherein the specimen holder is formed in the inner tube or the inner needle, and the optical window is formed in a wall portion of the outer tube.

6. The test apparatus according to claim 1,
wherein the optical window is disposed so that an optical axis of light that enters the optical window for optical detection or imaging intersects the optical window at two positions that are respectively on a distal side and on a proximal side of the specimen in a propagation direction of the light.

7. The test apparatus according to claim 6,
wherein the optical window is transmissive to light in a visible region or a near-infrared region.

8. The test apparatus according to claim 6,
wherein the optical window is transmissive to light in a wavelength range of 700 to 1400 nm.

9. The test apparatus according to claim 7,
wherein the optical window has a light transmittance that is 50% or greater.

10. The test apparatus according to claim 1,
wherein the optical window is disposed so that an optical axis of light that enters the optical window for optical detection or imaging intersects the optical window at one position that is on a proximal side of the specimen in a propagation direction of the light, and a reflection layer is disposed at a position that is on a distal side of the specimen in the propagation direction.

11. The test apparatus according to claim 2,
wherein at least one channel for introducing a measurement auxiliary liquid into the specimen holder or discharging the measurement auxiliary liquid from the specimen holder is formed in a wall surface of the tubular member.

12. The test apparatus according to claim 5,
wherein at least one channel for introducing a measurement auxiliary liquid into the specimen holder and at least one channel for discharging the measurement auxiliary liquid from the specimen holder are formed in the inner needle.

13. The test apparatus according to claim 12,
wherein the sum of areas of cross sections of the channels formed in the inner needle is less than 80% of an area of a cross section of the inner needle, and is preferably less than 50% of the area of the cross section of the inner needle, the cross sections being parallel to a short axis of the inner needle.

14. The test apparatus according to claim 1,
wherein a gap between the specimen and the optical window is filled with a refractive index matching liquid.

15. A method of observing a biopsy specimen, the method comprising:
holding the biopsy specimen with the specimen holder of the test apparatus according to claim 1; and
optically observing, by using the test apparatus claim 1, the biopsy specimen held by the specimen holder.

16. A method of observing a biopsy specimen sampled by a test apparatus, the method comprising:
optically observing a biopsy specimen, by using the test apparatus having:
a biopsy needle for sampling a biopsy specimen, wherein the biopsy needle includes a specimen holder that holds the sampled biopsy specimen, and
an optical window disposed in the specimen holder and configured to allow optical detection of the biopsy specimen,
wherein the biopsy specimen is held by the specimen holder,
wherein the biopsy needle includes a tubular member,
wherein the specimen holder is formed in a hollow portion of the tubular member, and the optical window is formed in a wall portion of the tubular member, and
wherein at least one channel for introducing a measurement auxiliary liquid into the specimen holder or discharging the measurement auxiliary liquid from the specimen holder is formed in a wall surface of the tubular member; and
causing the biopsy specimen held by the specimen holder to contact the measurement auxiliary liquid.

17. The method according to claim 16,
wherein the biopsy specimen held by the holder is observed at least once before the biopsy specimen contacts the measurement auxiliary liquid and at least once after the biopsy specimen has contacted the measurement auxiliary liquid.

18. The method according to claim 15,
wherein the optically observing the biopsy specimen is measuring the biopsy specimen by using a third-order nonlinear Raman microscope.

19. The method according to claim 18,
wherein the optical window is configured so that, in measurement performed by using the third-order nonlinear Raman microscope, aberration generated due to a difference in refractive indices when two laser beams used pass through the optical window is 10% or less.

20. The method according to claim 18,
wherein the Raman microscope is a stimulated Raman microscope.

* * * * *